United States Patent [19]

Fischer et al.

US005102804A

[11] Patent Number: 5,102,804
[45] Date of Patent: Apr. 7, 1992

[54] KARL-FISCHER REAGENT, KIT, AND A PROCESS FOR THE DETERMINATION OF WATER WITH THE AID OF THIS REAGENT

[75] Inventors: Wolfgang Fischer, Darmstadt; Gerhard Wieland, Bensheim; Karl-Dieter Krenn, Pfungstadt, all of Fed. Rep. of Germany

[73] Assignee: Merck Patent Gesellschaft Mit Beschrankter Haftung, Darmstadt, Fed. Rep. of Germany

[21] Appl. No.: 633,848

[22] Filed: Dec. 26, 1990

[30] Foreign Application Priority Data

Dec. 27, 1989 [DE] Fed. Rep. of Germany ....... 3943118

[51] Int. Cl.⁵ .......................................... G01N 33/18
[52] U.S. Cl. ................................ 436/42; 204/153.22; 422/61

[58] Field of Search ..................... 436/42; 204/153.22; 422/61

[56] References Cited

U.S. PATENT DOCUMENTS 4,385,124  5/1983  Verbeek et al. ............ 204/153.22 X
4,550,083 10/1985  Fisher et al. ........................... 436/42

Primary Examiner—Robert J. Hill, Jr.
Attorney, Agent, or Firm—Millen, White & Zelano

[57] ABSTRACT

The invention relates to a Karl-Fischer reagent, kit and a process for the determination of water with the aid of this reagent, which contains, instead of iodine, an approximately equimolar amount of iodine halides and salts of aromatic nitrogen-containing heterocyclic compounds.

16 Claims, No Drawings

KARL-FISCHER REAGENT, KIT, AND A PROCESS FOR THE DETERMINATION OF WATER WITH THE AID OF THIS REAGENT

BACKGROUND OF THE INVENTION

The invention relates to a modified Karl-Fischer reagent for the determination of water, which contains another iodine source instead of iodine, and to a process for the determination of water with the aid of this reagent.

Determination of water by the Karl-Fischer method and Karl-Fischer reagents for use therein are well known. See, for example, U.S. Pat. Nos. 4,748,122, 4,851,352 and 4,874,709. Conventional Karl-Fischer reagents contain, for example, sulfur dioxide, iodine and a base, e.g., pyridine, in a suitable solvent.

The main disadvantage in the customary Karl-Fischer method for the determination of water lies in the slow course of the reaction and the resulting laborious and lengthy titration. This is accompanied by limited storage time, unstable titre and the need for dark and cool storage. The iodine solutions to date are not stable in the customary plastic bottles because the bottles absorb iodine and in this way discolor.

Chemical Abstracts 67:25436t (1976) proposes replacement of the iodine solution in Karl-Fischer reagents by a solution of iodine bromide. A Karl-Fischer reagent containing iodine bromide exhibits practically the same stability on storage as a reagent prepared with iodine. Possibly for this reason, this proposal has not been accepted in practice.

An object of the invention is to provide a modified Karl-Fischer reagent which is stable, reacts rapidly, provides precise analytical results and exhibits an end point of maximum possible stability, even with a variable amount of water.

Upon further study of the specification and appended claims, further objects and advantages of this invention will become apparent to those skilled in the art.

Surprisingly, it has been found that such a Karl-Fischer reagent can be obtained if, instead of iodine, iodine halides are used together with salts of aromatic nitrogen-containing heterocyclic compounds, e.g., having 5- or 6-membered rings.

These substances are readily soluble in the reagent solution and such solutions are stable on storage and exhibit stable end points even in the case of titration over a wide water range. Since these solutions contain no elemental iodine, they can also be stored in plastic bottles without disadvantages.

The invention thus relates to a Karl-Fischer reagent for the determination of water, which is characterized in that, instead of iodine, the reagent contains approximately equimolar amounts of (1) an iodine halide or mixture thereof and (2) a slat of an aromatic nitrogen-containing heterocyclic compounds or mixture thereof.

The invention furthermore relates to a process for the determination of water with the aid of the Karl-Fischer reagent mentioned.

The invention further relates to a Karl-Fischer reagent kit comprising a solution containing sulfur dioxide and a base dissolved in a solvent and a titre containing (a) an iodine halide or mixture thereof, and (b) a salt of an aromatic nitrogen-containing heterocyclic compound or a mixture thereof. The invention also relates to a method of determining water using such a kit.

Surprisingly, it has been found that not only do the Karl-Fischer reagents according to the invention react more quickly than reagents containing iodine, they are also more stable than the known solutions containing iodine bromide by a factor of about 3.

Suitable iodine halides according to the invention are iodine chloride and iodine bromide. Suitable salts of aromatic nitrogen-containing heterocyclic compounds are the hydrohalides, preferably hydrochlorides and hydrobromides, of pyridine, imidazole and alkyl or phenyl derivatives thereof. The iodine halides and the salts of the aromatic nitrogen-containing heterocyclic compounds should be present in approximately equimolar amounts, that is to say in a ratio of about 0.8 to 1.2:1, preferably about 1:1.

The total molar amount of iodine halide(s) and salt(s) of aromatic nitrogen-containing heterocyclic compounds is, for example, substantially equivalent to the concentration of iodine used in conventional Karl-Fischer reagents.

Solvents suitable for both dissolving the sample to be analyzed for its water content and for the titrating agent are all the solvents described for this purpose in the literature, preferably alcohols and/or glycols, in particular lower alcohols, such as methanol, ethanol, propanol and the like, as well as ethylene glycol and ethylene glycol monoalkyl ethers, or diethylene glycol monoalkyl ethers and propylene glycol monoalkyl ethers. Butyrolactone, for example, is also a most suitable solvent for the reagent according to the invention. The solvents can be used individually or in any desired mixing ratio.

The Karl-Fischer reagent according to the invention is preferably present as a so-called one-component reagent which contains all the constituents in a single solution. The one-component reagent is particularly advantageous if the substance to be analyzed is more readily soluble in a solvent other than the solvent of the reagent. In this case, the rate of reaction does not depend on the rate of solution either. It is of course also possible for the Karl-Fischer reagent according to the invention to be employed as a so-called two-component reagent which then comprises two solutions, a solvent and a titrating agent. The solvent contains sulfur dioxide, a base such as pyridine or a customary pyridine substitute in a solvent and is used to take up the sample to be analyzed for its water content. The titrating agent is a solution, adjusted to a constant titre, of the mixture according to the invention of iodine halide and a salt of an aromatic nitrogen-containing heterocyclic compound in a solvent.

Using the Karl-Fischer reagent according to the invention, the end point of the determination of water by volumetric analysis can be determined visually, photometrically or electrometrically (dead-stop method, coulometric method). The reagent is suitable either for use in titrating machines or as a field method. The titration is in general carried out with exclusion of atmospheric humidity. Electrometric titration, in particular the so-called dead-stop method, is currently preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 39 43 118.5, filed Dec. 27, 1989, is hereby incorporated by reference.

EXAMPLES

Example 1

To prepare a titrating solution, 23 g of imidazole are dissolved in 1 l of methanol, and 12 g of hydrogen chloride are passed in. 55 g of iodine monochloride are then added and dissolved.

The factor of this solution is 5.71 (i.e. F=5.71), that is to say 1 ml of the solution indicates 5.71 mg of water.

Example 2

To prepare a titrating solution, 39 g of pyridinium chloride and 70 g of iodine monobromide are dissolved successively in 1 l of methanol, while stirring. F=5.24.

Example 3

To prepare a titrating solution, 91 g of the iodine chloride addition product of imidazole hydrochloride are dissolved in 1 l of butyrolactone. F=5.32.

Example 4

A comparison experiment was carried out with the Karl-Fischer processor 658 from Metrohm. The titration was carried out with the Karl-Fischer titrating solution according to Example 1. An equimolar solution of iodine in methanol was used as the comparison solution.

In both cases, 30 ml of a solvent which consisted of 25 ml of ethylene glycol monomethyl ether and 5 ml of a pyridine-containing sulfur dioxide solution of methanol (9 g of sulfur dioxide and 35 g of pyridine per 100 g of solution) were used as the starting substance. The solvent was titrated to the end point. 25 mg of water were then added and the mixture was titrated to the end point again. The times for the titration of this 25 mg of water were:
solution according to Example 1: 135 seconds
iodine solution: 220 seconds The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A Karl-Fischer reagent for the determination of water, comprising, in approximately equimolar amounts, (a) an iodine halide or mixture thereof, and (b) a salt of an aromatic nitrogen-containing heterocyclic compound or mixture thereof.

2. A Karl-Fischer reagent according to claim 1, wherein said salt or mixture thereof is a hydrohalide of pyridine or a mixture thereof, or a hydrohalide of imidazole or a mixture thereof.

3. A Karl-Fischer reagent according to claim 2, wherein said hydrohalide is hydrochloride or hydrobromide.

4. A Karl-Fischer reagent according to claim 1, wherein said iodine halide or mixture thereof is iodine chloride.

5. A Karl-Fischer reagent according to claim 1, wherein said iodine halide or mixture thereof is iodine bromide.

6. A Karl-Fischer reagent according to claim 1, wherein (a) and (b) are in a ratio of about 0.8-1.2:1.

7. A Karl-Fischer reagent according to claim 1, wherein said salt or mixture thereof is an alkyl derivative of a pyridine hydrochloride or a mixture thereof, or a phenyl derivative of a pyridine hydrohalide or a mixture thereof.

8. A Karl-Fischer reagent according to claim 7, wherein said hydrohalide is hydrochloride or hydrobromide.

9. A Karl-Fischer reagent according to claim 1, wherein said salt or mixture thereof is an alkyl derivative of a imidazole hydrohalide or a mixture thereof, or a phenyl derivative of imidazole hydrohalide or a mixture thereof.

10. A Karl-Fischer reagent according to claim 9, wherein said hydrohalide is hydrochloride or hydrobromide.

11. A Karl-Fischer reagent according to claim 1, wherein components (a) and (b) are dissolved in a solvent.

12. A Karl-Fischer reagent according to claim 11, wherein said solvent is butyrolactone.

13. A Karl-Fischer reagent according to claim 11, further comprising sulfur dioxide and a base dissolved in said solvent.

14. In a method of determining water using a Karl-Fischer reagent, the improvement comprising employing a Karl-Fischer reagent according to claim 1.

15. A Karl-Fischer reagent kit comprising:
a solution containing sulfur dioxide and a base dissolved in a solvent, and
a titre containing (a) an iodine halide or mixture thereof, and (b) a salt of an aromatic nitrogen-containing heterocyclic compound or mixture thereof.

16. In a method of determining water using a Karl-Fischer reagent kit, the improvement comprising employing a Karl-Fischer reagent kit according to claim 15.

* * * * *